United States Patent
McIntosh

(10) Patent No.: US 6,842,018 B2
(45) Date of Patent: Jan. 11, 2005

(54) PLANAR CAPACITIVE TRANSDUCER

(76) Inventor: Robert B. McIntosh, 2432 Tram Rd., New Bern, NC (US) 28562

( * ) Notice: Subject to any disclaimer, the term of this patent is extended or adjusted under 35 U.S.C. 154(b) by 8 days.

(21) Appl. No.: 10/425,625

(22) Filed: Apr. 30, 2003

(65) Prior Publication Data
US 2003/0214310 A1 Nov. 20, 2003

Related U.S. Application Data
(60) Provisional application No. 60/378,857, filed on May 8, 2002.

(51) Int. Cl.[7] .......................... G01R 27/26; G01N 19/00
(52) U.S. Cl. ..................... 324/664; 324/658; 73/335.04
(58) Field of Search ............................... 324/663, 664, 324/658–662; 73/73, 74, 29.01, 29.02, 335.01, 335.02, 335.03, 335.04, 335.05; 526/250–254

(56) References Cited

U.S. PATENT DOCUMENTS

| 4,891,574 A | * | 1/1990 | Nagaya et al. | ............... 324/664 |
| 4,968,946 A | * | 11/1990 | Maier | .......................... 324/671 |
| 5,045,828 A | * | 9/1991 | Kulwicki et al. | .............. 338/35 |
| 5,208,544 A | * | 5/1993 | McBrearty et al. | ......... 324/687 |
| 5,767,687 A | * | 6/1998 | Geist | ........................... 324/664 |
| 6,126,312 A | * | 10/2000 | Sakai et al. | ..................... 374/28 |
| 6,700,394 B2 | * | 3/2004 | Greer | .......................... 324/686 |

* cited by examiner

Primary Examiner—Anjan Deb
Assistant Examiner—Jeff Natalini

(57) ABSTRACT

A transducer comprising at least one planar capacitor with a thin coverlayer of material selected to maximize electric field coupling between cooperating capacitor electrodes within a region external to a principal surface of the coverlayer. Preferred coverlayer materials have low values of moisture absorption, surface free energy, permittivity, dielectric dissipation, and electrical conductance. According to one embodiment of the invention, a driven shield further enhances electric field coupling over and in a region external to the principal surface. The transducer also can promote a physical change in specific adsorbates and materials and simultaneously detect and measure an effect of the induced change. Applications for the transducer of the invention include the measurement of the moisture content of grain and bulk stored commodities, humidity, a dew point temperature, the onset of condensation and rates of adsorption and desorption.

19 Claims, 8 Drawing Sheets

PLANAR CAPACITIVE TRANSDUCER

CROSS-REFERENCE TO RELATED APPLICATION

This application claims priority from U.S. Provisional Application No. 60/378,857, filed May 8, 2002, the entire contents of which are hereby incorporated by reference.

FIELD OF THE INVENTION

The present invention relates to capacitance transducers that measure moisture, humidity, permittivity, dielectric dissipation, and states of electrical polarization of materials absorbed on and residing within a region external to a principal surface.

BACKGROUND OF THE INVENTION

Prior-art capacitive moisture and humidity sensors detect a change in capacitance due to a change in permittivity of a porous material layer due to cyclic absorption and desorption of water vapor. A disadvantage of these sensors is a slow response due to a time required for bulk material to reach equilibrium with water vapor in an external environment. Accordingly, the design of existing electrical hygrometers is constrained by a trade off between sensitivity and acceptable response time. Other disadvantages are a loss of calibration, reduction of sensitivity, and failure due to material absorption and surface retention of contaminants including fluids and particulates.

U.S. Pat. No. 6,222,376 B1 of Tenney, III and U.S. Pat. No. 4,429,343 of Freud disclose humidity sensors with interdigitated capacitor electrodes that are less sensitive to surface contamination. For these transducers, a majority of electric field coupling between the capacitor electrodes resides inside the material of the transducer. However, this approach further constrains sensor response time and does not provide a capability for reliable operation in an environment of fine airborne particulates.

Prior-art capacitance-based instruments used to measure the moisture content of agricultural products require a sample of fixed volume to be placed in a measurement cell. The permittivity or dielectric constant of the sample is then measured by a parallel-plate capacitor and a value of moisture content is determined from calibration data. The temperature dependency of permittivity is compensated for by measuring the temperature of the sample. Standard calibration curves of moisture content vs. dielectric constant at different temperatures exist for many agricultural products and industrial materials.

The density and packing fraction of grain and granular products strongly influence a measured value of permittivity. Small-volume samples are loosely packed and packing density can vary from sample-to-sample. This uncertainty is avoided in part by capacitive moisture instruments that simultaneously weight a measurement sample when its volume is known. These prior-art instruments are expensive and are not configured to provide in-situ measurements of commodities stored in bins, silos, and hoppers.

Humidity is the most important and difficult to control environmental parameter in greenhouses, particularly at high levels where the partial pressure of water vapor approaches saturation. Humidity affects the quality, yield, and health of plants. Greenhouse management is generally concerned with the control of relative humidity (RH) and vapor pressure deficit (VPD). RH is primarily used for disease control and VPD is used for transpiration control. Psychrometers with wet and dry elements are generally the only practical instruments available to measure high levels of humidity and to determine VPD in greenhouses and fog houses. They are too expensive and complex to be deployed in the numbers necessary for multi-zone climate control.

A critical concern in greenhouse management is to prevent the formation of freestanding water on plant surfaces and to prevent condensation from dripping on leaves. Accordingly, a need exits for networks of low-cost, chemically resistant condensation alarms.

A well known practice in the art of moisture and humidity measurement is to control the temperature of a transducer with a heating element or a thermoelectric heating and cooling module. This practice can enhance measurement accuracy and extend a range of measurement.

DEFINITIONS

Planar Capacitor—Designation used herein to identify a capacitor with electrodes formed in a metal film deposited or laminated to an insulating baselayer. Planar capacitors are constructed with cooperating interdigitated electrodes or more simply with parallel stripline conductors.

Planar Capacitive Transducer—Designation used herein to identify a transducer that includes at least one planar capacitor.

Principal Surface—Designation used herein to identify an exposed surface of a coverlayer of a planar capacitive transducer.

Driven Shield—Designation used herein to identify an electrode formed under and insulted from the electrodes of a planar capacitor. A voltage applied across the electrodes of a planar capacitor is also applied to the driven shield to minimize electric field coupling and associated fixed capacitance within and below a baselayer over which the capacitor electrodes are formed.

Measurement Reach—Designation defined herein to identify an effective distance over which a measurement can be made in a region extending from a principle surface of a planar capacitive transducer.

SUMMARY

A general objective of the present invention is to provide a capacitive transducer with a construction that provides a new capability method to detect and measure objects including moisture and humidity. The disclosed transducer includes a planar capacitor with a thin coverlayer of material with low values of moisture absorption, surface free energy, permittivity, dielectric dissipation, and electrical conductance. Contrary to prior art moisture and humidity sensors, the coverlayer material is selected to maximize electric field coupling over a principal surface and in a region external to the surface. Since moisture is not absorbed in a material layer, transducers of the present invention exhibit a nearly instantaneous response to a change in moisture or humidity.

Another objective of the invention is to use an active shield to enhance electric field coupling in an external region of measurement to increase capacitance sensitivity and extend measurement reach. The active shield minimizes electric field coupling and associated fixed values of capacitance in a baselayer, substrate, and support structure.

Another objective of the present invention is to provide a transducer with a capability to evaluate the kinetics and mechanisms of nucleation, polarization, changes of phase and crystalline order of certain adsorbed material films on a principal surface of measurement.

Another objective of the present invention is to promote a physical change of a state of polarization, phase, or crystal orientation of an adsorbate or film deposited on a low energy surface while simultaneously detecting and measuring an effect of the induced change.

Still another objective is to provide thin flexible humidity and moisture transducers that can be bonded to a flat surface, and to outside and inside surfaces of a tube of common material;

One embodiment of the invention includes a heater element to maintain or control rates of adsorption on and desorption from a principal surface.

Another embodiment of the invention includes a thermoelectric heating and cooling module to perform for example the functions of a self-calibrating chilled hygrometer to measure a dew point.

Still another embodiment of the present invention includes a capacitive transducer with a principal surface that is activated to increase or decrease surface free energy. Specific applications of economic importance for the transducers of the present invention include, but are not limited to:

1. Improved chemically resistant transducers to measure the moisture content of bulk stored agricultural and industrial products; to control milling, drying, and baking systems; and to control moisture sensitive manufacturing processes;
2. Improved transducers to measure the moisture content of soils for crop irrigation, orchard management, and hydrology;
3. Improved transducers to measure humidity to high levels approaching saturation.
4. A low-cost, chemically resistant alarm that detects the onset of condensation;
5. Improved rapid response transducers to measure moisture in industrial gas and fuel lines and to monitor the humidity of air drawn into intakes of combustion engines.

Additional applications are for the transducer of the present invention are expected to arise because of its unique construction and principle of operation. All embodiments can include a thermistor, thin-film temperature sensor, or semiconductor circuit to measure temperature.

Many high-volume markets for the transducer of the present invention are highly sensitive to cost. Accordingly, it is desirable the transducers be manufactured with low-cost materials using conventional processes and equipment employed by the flexible circuit and printed-circuit board industries. Small transducers can be fabricated in high volume by processes employed by manufacturers of semiconductor integrated circuits.

The above and still other objects and advantages of the present invention will become apparent from consideration of the following description and drawings.

BRIEF DESCRIPTION OF THE DRAWINGS

The embodiments of the invention are described by way of non-limiting drawings. The drawings are schematic in nature for clarity of description and thus features shown are not drawn to relative scale; like reference numbers designate similar parts or elements with similar functions.

DESCRIPTION

General Description and Principles of Operation

Figure 1:
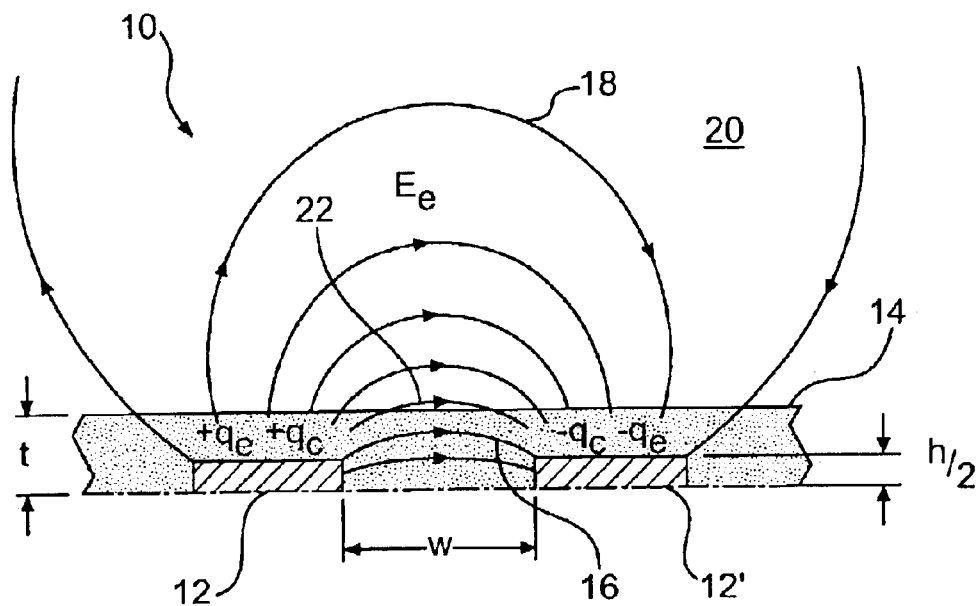
FIG. 1 is a sectional view of a top half-plane of a simple planar capacitor.

The general construction and advantages of the transducer of the present invention are first described below with reference to FIGS. 1 and 2. FIG. 1 is a sectional view of a top half-plane of a simple planar capacitor generally shown by reference number 10 comprising two, parallel strip electrodes 12 and 12' with an edge-to-edge spacing w. A coverlayer 14 of thickness t is laminated over electrodes 12 and 12' of total thickness h, or h/2 as shown in this half-plane view. When a voltage V is applied across electrodes 12 and 12', surface charge q of opposing polarity is induced on the cooperating electrodes with a magnitude equal to the product CV, where C is a capacitance value of capacitor 10.

In FIG. 1, surface charge q is shown comprising two components: $q_c = \rho_c A_c$ and $q_e = \rho_e A_e$, where $\rho_c$ and $\rho_e$ are surface charge densities of effective electrode surface areas $A_c$ and $A_e$ of capacitor 10. Lines of force 16 between charges $\pm q_c$ substantially determine the electric field strength in coverlayer 14 and lines of force 18 between charges $\pm q_e$ substantially determine the electric field strength $E_e$ in an external region 20. Although line of force 22 has a substantial path length in both media, it is disregarded for the purpose of a simple description. However, charge associated with line of force 22 can be accounted for by incremental additions to charges $q_c$ and $q_e$.

The capacitance C of capacitor 10 for a potential difference V applied across electrodes 12 and 12' can be expressed as $$C = \frac{\rho_c A_c + \rho_e A_e}{V} \quad (1)$$

EQU. 1 can alternately be expressed as, $$C = \frac{\epsilon_c E_c A_c + \epsilon_e E_e A_e}{V} = C_c + C_e \quad (2)$$

where $\epsilon_c$ and $\epsilon_e$ are permittivities (dielectric constants) and $E_c$ and $E_e$ are the effective electric field intensities in coverlayer 14 and external region 20 respectively. Capacitances $C_c$ and $C_e$ are capacitances due to electric field coupling and permittivities in the respective media.

The advantages of transducer of the present invention are apparent from FIG. 1 and EQU. 2. The transducer measures or detects a change in permittivity $\epsilon_e$ or electric field $E_e$ in medium 20. It is evident, to maximize capacitance sensitivity $S=\Delta C_e/(C_c+C_e)$ of capacitor 10, it is desirable to maximize $\in_e E_e A_e$ with respect to $\in_c E_c A_c$. This can be accomplished by reducing $\in_c$, thickness t of coverlayer 14, and to a lessor degree the thickness h of electrodes 12 and 12'.

Figure 2:
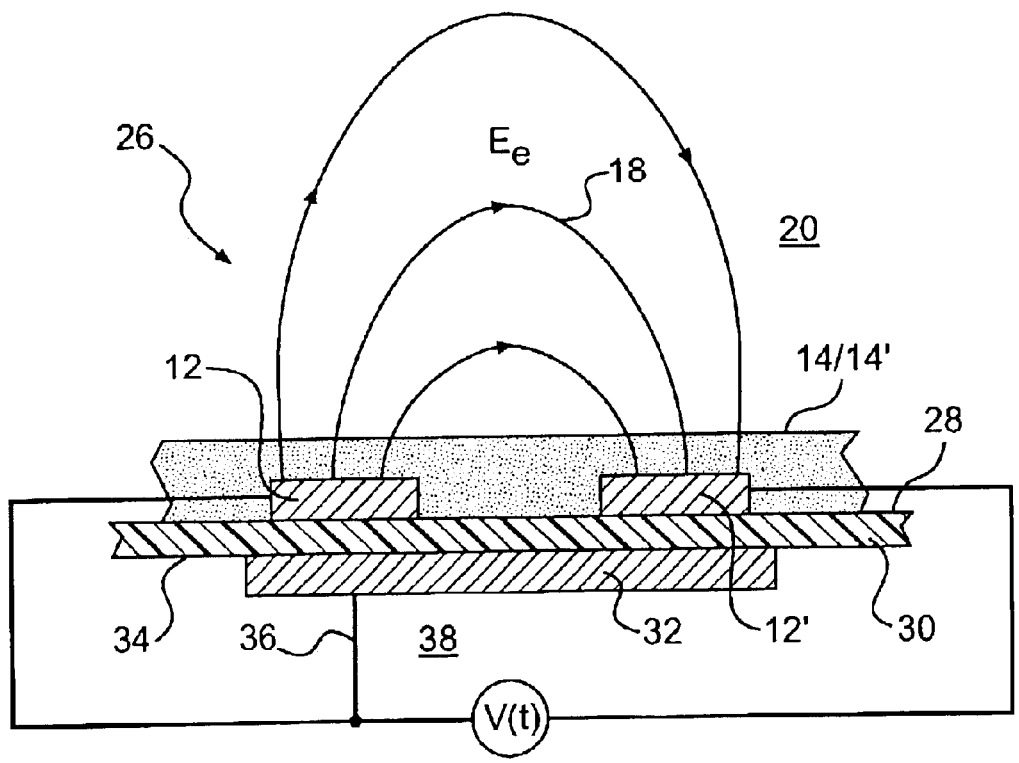
FIG. 2 is a sectional view of a simple planar capacitor with a driven shield.

FIG. 2 is a sectional view of a simple planar capacitor generally shown by reference numeral 26 with stripline electrodes 12 and 12' formed on a first surface 28 of a baselayer 30. A coverlayer 14 with a principal surface 14' is formed over electrodes 12 and 12'. A driven shield 32 is formed on a second surface 34 of baselayer 30 under electrodes 12 and 12'. A time varying excitation voltage V(t) is applied across electrodes 12 and 12' to provide a capability to measure the capacitance of capacitor 26 that is a function of the permittivity of media residing in region 20. When this same voltage V(t) is applied to shield 32 by conducting lead 36, electric field coupling and associated fixed capacitance are minimized in baselayer 30 and a region 38 below electrodes 12 and 12', thereby decreasing $\in_c E_c A_c$ and the value of $C_c$ and thereby C in EQU. 2. This causes capacitor 26 to become more dependent upon and sensitive to the values and changes of $\in_e$ and $E_e$ in region 20.

Accordingly, the material of coverlayer 14 is selected with properties that minimizes its influence in the measurement of a physical object or effect in region 20 external to principle surface 14'. This objective is generally achieved with a coverlayer material that has low values of moisture absorption, surface free energy, permittivity, dielectric dissipation, and electrical conductance. Many low-dielectric materials exhibit these properties, most notably fluoropolymers, chloropolymers, chlorofluoropolymers, and polyparaxylene.

Figure 3:
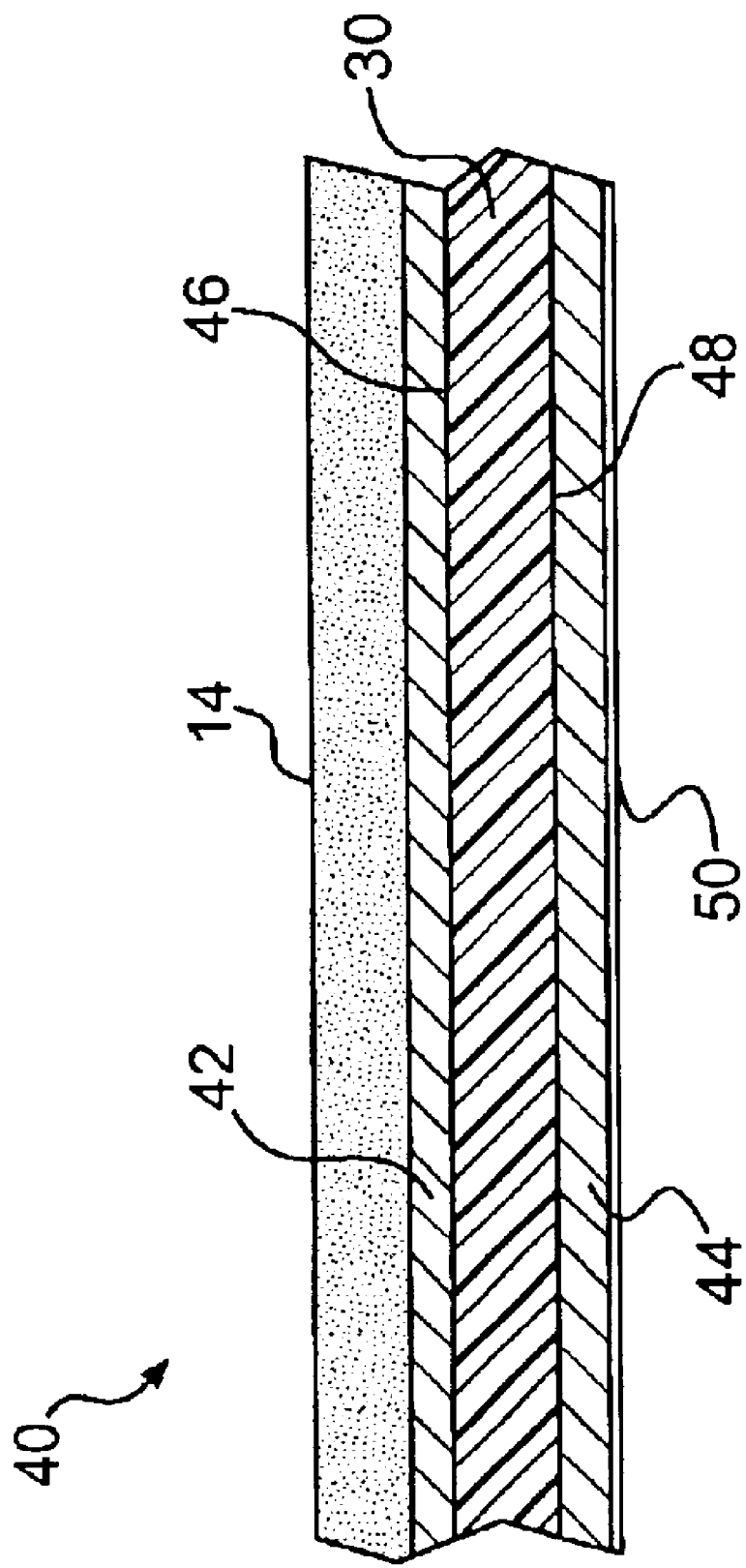
FIG. 3 is a partial sectional view of the material layers of a planar capacitor.
Figure 4A:
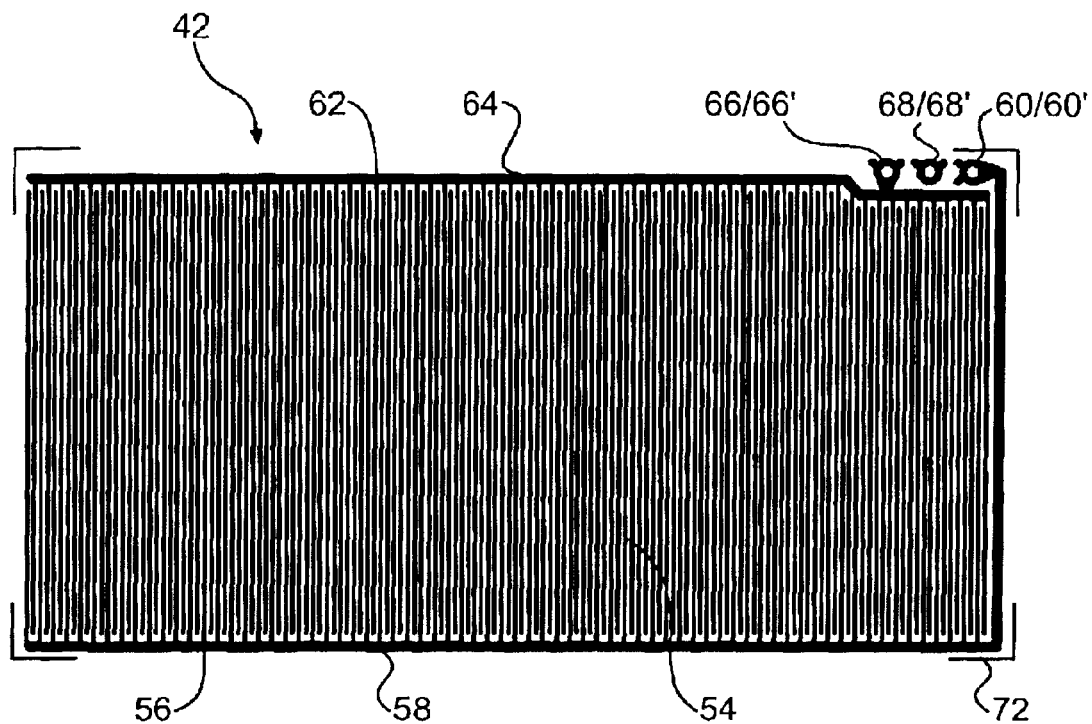
FIG. 4A is a top view of a first metal layer of a planar capacitor.
Figure 4B:
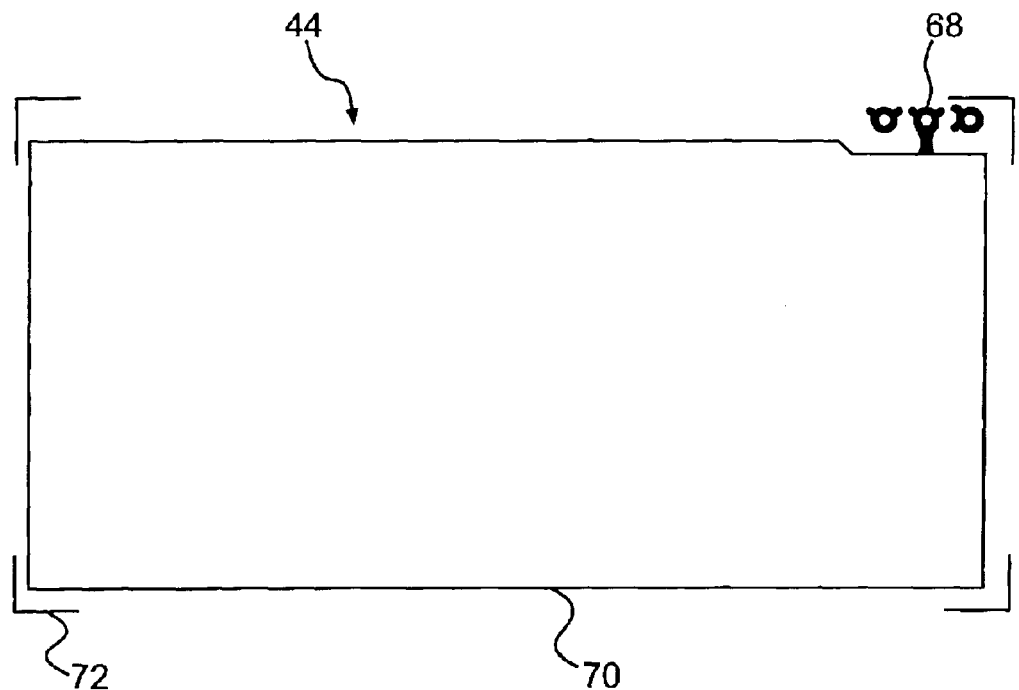
FIG. 4B is a top view of a second metal layer of a planar capacitor with a driven shield.

FIG. 3 is a sectional view identifying the general material layers of a planar capacitor with a driven shield generally shown by reference numeral 40. A first and second metal layer 42 and 44 of ½ oz. copper foil are laminated to top and bottom surfaces 46 and 48 of a 0.002" thick polyimide baselayer 30 respectively. At least one pair of cooperating interdigitated electrodes is etched in metal layer 42 and a driven shield is etched in metal layer 44 as shown in FIGS. 4A and 4B. A low dielectric and low moisture absorbing coverlayer 14 is formed over metal layer 42. A corrosion limiting layer 50 of a material such as tin or silver is applied to metal layer 46 by a hot dip or electroless plating process. Metal layer 44, with or without film 50, can be affixed to a surface of a thin-film heater element or to a surface of a thermoelectric heating and cooling module to provide a means for temperature control.

It should be obvious to persons skilled in the art of integrated circuit manufacturing that the electrode geometry and material film thicknesses of planar capacitors 10, 26, and 40 can be fabricated with micrometer size dimensions.

Operational Modes and Limitations

The modes of operation and measurement limitations of the transducers of the present invention are dependent in part upon the behavior of physical adsorption on low energy films and coatings. It has been determined by measurements with the disclosed transducer that a low free-energy surface of a fluoropolymer does not prevent the adsorption and condensation of water at partial pressures of water vapor approaching saturation. At high values of RH, clusters of monolayer molecules are believed to form nucleation sites that promote the formation of additional layers of condensation. After a first monolayer of water forms, a cascade of new layers condense as the partial pressure of water vapor approaches saturation. Strong electrical coupling within an adsorbed film of water causes the capacitance of a transducer to abruptly increase by 100% and over a 10% range of RH after the onset of adsorption. This is due in part to the high dielectric constant of water that is substantially 79 at 23° C. compared to values of 2.1 to 3.0 for typical coverlayers of the transducer of the invention and in part due to the higher surface energy of a first layer of water compared to the underlying principal surface.

Based upon data obtained with high resolution capacitance measurement electronics, it was found that water molecules can be detected electrically during an early stage in the formation of a first distinct monolayer, a level below one that can be detected optically by a chilled mirror hygrometer.

Stored grain and other granular commodities have a moisture content that depends upon the temperature and RH of surrounding air. It is common to report moisture content in terms of equilibrium moisture content (EMC). EMC can be related to the percentage of water by weight in a product and to the equilibrium relative humidity (ERH) of a product. ERH is the RH that air reaches in intergranular regions when it is in thermodynamic equilibrium with grain with a specific moisture content and temperature. The transducer of the invention is a highly sensitive and fast responding sensor of moisture in bulk materials at values of ERH below the adsorption threshold of a principal surface. This well behaved region of substantially linear operation can be extended to higher levels of ERH by thermally biasing the threshold of adsorption (onset of adsorption) by affixing transducer 10 or 26 to a thin-film heating element. A small temperature increase above ambient shifts the threshold of adsorption and region of extreme capacitance change to higher levels of humidity.

The dielectric constant of bulk commodities are highly dependent on packing density and to a lessor extent on temperature. Air and water vapor residing within the voids and passages of granular materials do not significantly contribute to the total permittivity of the material. When a planar capacitive moisture transducer of the present invention is placed within a mass of grain to a specified depth, variations in capacitance are small as the overburden pressure causes substantially uniform packing density.

For grain with ERH levels of less than 75% to 85%, multiple moisture readings with transducers of the present invention have been found to be nearly instantaneous and repeatable within 0.2% and stable to 20 ppm (0.0002%). Similar results were obtained in still air when substantially no water is adsorbed on a principal surface of the transducer. Grain with a moisture content corresponding to an ERH of 75% generally exceed specified market limits. Above these moisture levels, molds and fungus quickly develop at the typical temperatures of storage and transport.

Capacitance changes with RH in air external to the coverlayer of the transducer are low because of the small quantity of water that exists as a vapor. However, values of RH greater than 10% can generally be measured to high accuracy using the capacitive bridge circuits identified below. The response time of disclosed a capacitive transducer to changes in moisture and humidity is limited by the response of electrical measurement means. Response times of milliseconds and less are typical.

For measurements of RH above the threshold of adsorption on a low-energy coverlayer, the capacitive change of the transducer is so extreme that it is desirable to limit the measurements to a narrow range of RH. This can be accomplished by lowering the surface energy or by increasing the temperature of the coverlayer to bias the onset of adsorption to a partial pressure of water vapor equivalent to a RH value of 90% or more.

The adsorption discontinuity of a many low dielectric surfaces and the vapor pressure at which it occurs can be sensed by the transducer of the invention to provide a simple, low-cost condensation alarm. Those skilled in the art of chilled-mirror hygrometry will recognize a capability also exists to electrically measure a dew point temperature when the transducer of the present invention is mounted on a surface of a thermally controlled thermoelectric heating and cooling module. An advantage of measuring a dew point by chilling a low-energy surface is that the free energy of the surface and corresponding temperature of condensation more closely match the values of plant leaves and many dielectric materials.

The free energy of a principal surface of the present invention can be modified by activating the surface by a chemical treatment, a plasma, or a corona discharge. These processes are used commercially to improve the adhesive bonding properties of low surface energy plastics. Within this specification, the definitions of surface activation and active surface are extended to include processes that also lower the free energy of a surface such as a chemical treatment, vapor deposition, and implantation of charged particles. Surface activation as defined herein provides a means to either increase or decrease the partial vapor pressure at which an abrupt change in capacitance occurs when an adsorbate starts to physically bond to a principal surface of a coverlayer of the instant invention at a given temperature, For certain surface conditions and electric field strengths, it has been inferred by measurements made with transducers of the present invention that polar water molecules adsorbed on a low energy surface are highly unstable and mobile. The molecular dipoles align themselves with the electric field of a periodic voltage applied to the capacitor electrodes by capacitance measurement means. When the voltage is removed, the polar molecules return to an initial minimum energy state. Measurement means that apply a periodic voltage across the capacitor electrodes include RC relaxation oscillators and AC bridge circuits.

Electrically induced motion of water molecules on the low energy surfaces of planar capacitors 12 and 26 of FIGS. 1 and 2 significantly increase dielectric dissipation in the capacitors. When a RC relaxation oscillator is used to measure capacitance, a change in an amount of an adsorbate generally results in a decrease in frequency. If the surface energy of the coverlayer is sufficiently low, the reorientation of polar molecules dissipate energy as characterized by capacitance dissipation and dielectric hysteresis. This change in polarization causes a large change in the duty cycle of an RC relaxation oscillator. It takes a longer period of time to charge a capacitor through a resistor or by a current source when the polarization of a capacitor dielectric increases with an applied voltage.

Planar capacitor transducers constructed with a coverlayer of a copolymer of vinylidenefluoride and chlorotrifluoroethylene have low values of capacitive dissipation that do not significantly increase with a quantity of adsorption of water. However, the principal surface of the copolymer coverlayer can be chemically activated by exposure to acetone. It was found that this chemical treatment increased capacitance and caused an adsorbed water film to strongly polarize in an electric field associated with the charging portion of an applied periodic voltage. Capacitance dissipation due to cyclic polarization increased the duty cycle of the squarewave output of a 20-kHz, RC oscillator output from substantially 50% to values exceeding 2000%. The ability to activate or electrically change the surface energy of a dielectric coverlayer suggests the transducer of the present invention has a capability to evaluate the kinetics and mechanisms of nucleation, polarization, phase changes, and crystalline order of certain adsorbates on a low-energy surface.

Accordingly, within the limitations identified hereinabove, the transducer of the present invention has the capability to make accurate and rapid measurements of objects including moisture, humidity, a vapor, a fluid, a contaminant, a dew point, a fluid level, states of polarization, rates of adsorption and desorption, a displacement, proximity of an object, and a local electric field.

Thin flexible embodiments of the present invention can be adhesively bonded to a flat surface and to outside and inside surfaces of a tube of common materials. For these installations, electrode spacing can be increased while proportionately increasing the area of the planar capacitor. Wider electrode spacing provides a longer path over which an electric field is coupled, thereby providing a deeper measurement reach. A extended measurement reach also increases the range of proximity detection and the distance over which a local electric field can be sensed. Larger surface areas provide a larger volume in which to acquire an average measurement of moisture for granular commodities such as corn and wheat.

For many applications, the size of the surface area of a thin-film transducer is not restricting, e.g., when bonded to a inside wall of a wide HVAC duct or plenum.

A capacitance liquid level sensor or fuel gauge can be fabricated with the simple structure of planar capacitors 10 and 26 of FIGS. 1 and 2 with parallel stripline electrodes 12 and 12'.

Detailed Design of Select Embodiments

FIG. 4A is a top view of first metal layer 42 of capacitor 40 of FIG. 3. Capacitor electrodes generally shown by reference numeral 54 comprise interdigitated fingers etched in metal layer 42. A first planar capacitor electrode comprises a set of fingers 56 connected to a ground bus 58 connected to a wire point pad 60 with a plated through hole 60'. A cooperating capacitor electrode comprises a second set of fingers 62 connected to a sensing bus 64 connected to a wire point pad 66 with a plated through hole 66'. Capacitor 40 is measured by connecting capacitance measurement electronics means between pads 60 and 66. A third wire point pad 68 with a plated through hole 68' is used to connect an electrical signal to a driven shield 70 etched in a second metal layer 44 shown in FIG. 4B. Capacitor 40 is die-cut to dimensions defined by registration marks 72. The width and spacing of fingers 56 and 62 for flexible circuit embodiments of the transducer can range between 0.001 and 0.006 inch. Interdigitated electrodes with much smaller dimensions can be lithographically patterned and etched on other dielectric films and substrates.

The electrode geometry of planar capacitor 40 can be shrunk by an order of magnitude and more to provide low-cost sensors with a rapid response to control residential environments, home appliances, automotive interiors, and HVAC systems.

FIG. 4B is a top view of second metal layer 44 of planar capacitor 40. Metal layer 44 comprises driven shield 70 connected to wire point pad 68. When shield 70 is actively driven by the circuit arrangement shown in FIG. 5 (wherein the driven shield is identified by numeral 108) the effective capacitance of capacitor 40 is reduced by 30% or more due to a reduction in electric field coupling within and below a 0.002 polyimide baselayer 30 for a 6-Volt excitation voltage.

Figure 5:
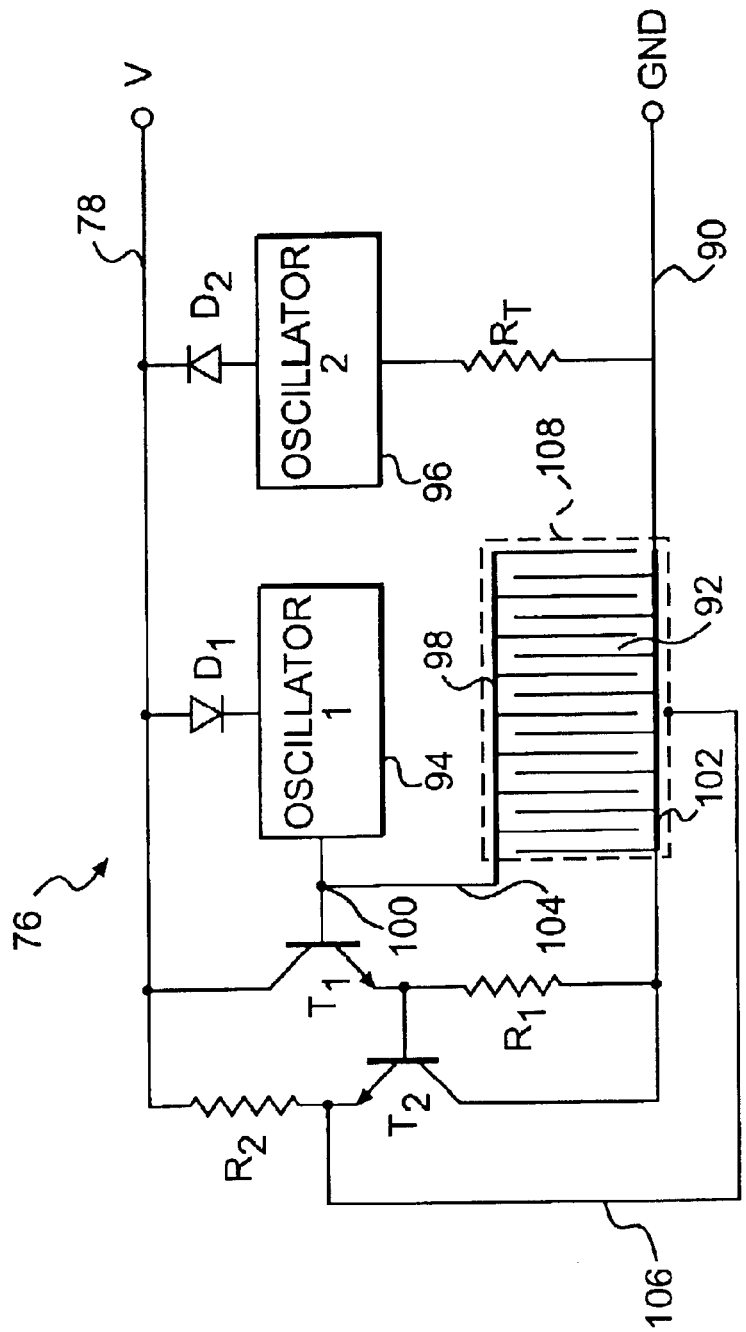
FIG. 5 is a simplified electrical block diagram of a moisture/temperature transducer.
Figure 5:
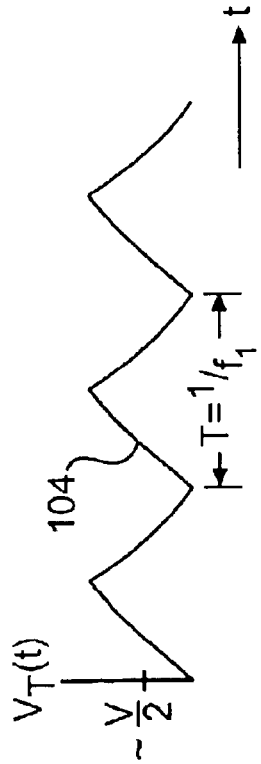
Figure 6A:
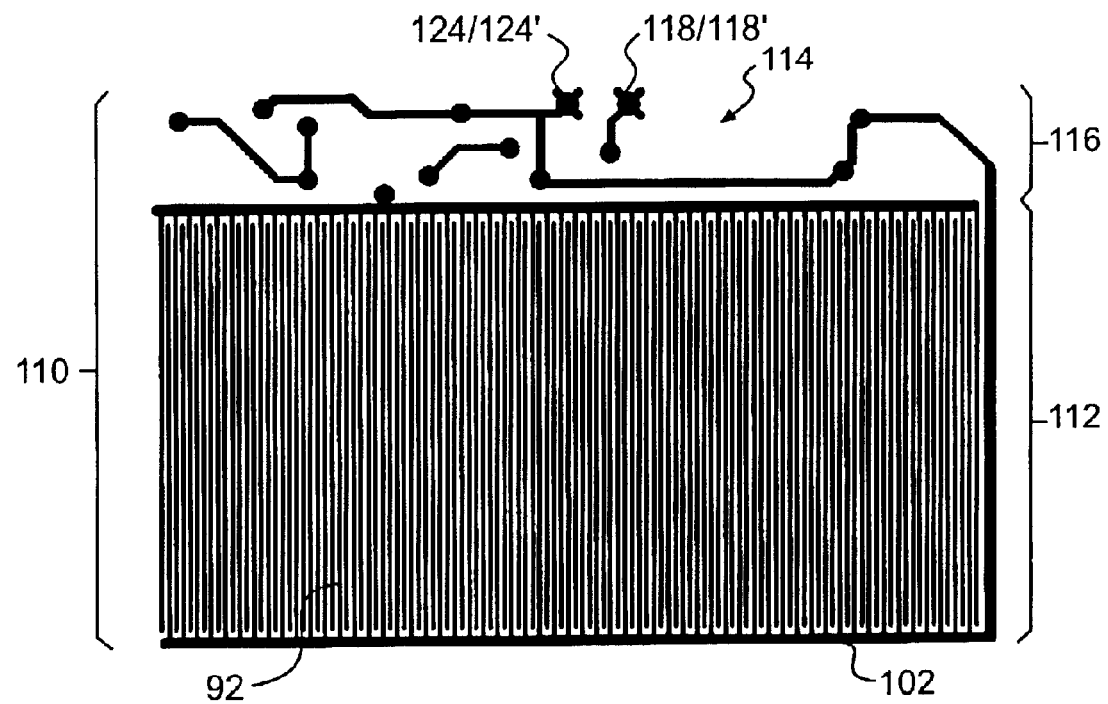
FIG. 6A is a top view of a first metal layer of a flexible printed circuit transducer.
Figure 6B:
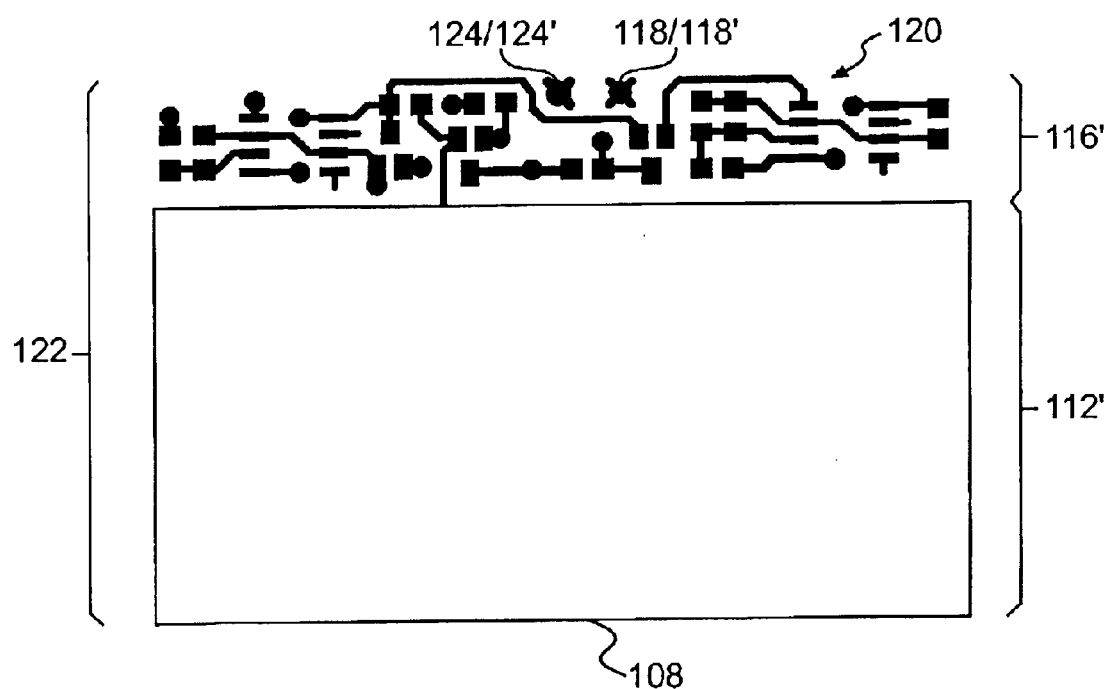
FIG. 6B is a top view of a second metal layer of a flexible printed circuit transducer.

FIG. 5 is a simplified electrical block diagram of a combination moisture/temperature transducer generally shown by reference numeral 76 fabricated as flexible printed circuit with metal layers 110 and 122 of FIGS. 6A and 6B. For convenience, this specific embodiment requires only two electrical connections for operation and transmission of moisture and temperature output signals: a supply line 78 connected to a voltage V of switchable polarity and a conducting trace 90 connected to ground or a reference potential. Transducer 76 includes a planar capacitor 92; a first and a second RC relaxation oscillator 94 and 96; a thermistor $R_T$; and steering diodes $D_1$ and $D_2$. Diodes $D_1$ and $D_2$ connect oscillators 94 and 96 respectively to supply line 78. A sensing electrode 98 of planar capacitor 92 is connected at node 100 connected to comparator inputs of oscillator 94. A ground electrode 102 of capacitor 92 is connected to trace 90. Thermistor $R_T$ is connected between comparator inputs of oscillator 96 and trace 90.

When a voltage +V is applied to supply line 78, oscillator 94 is activated and oscillates at a square wave frequency $f_1$ inversely proportional to a capacitance value C of capacitor 92. Frequency $f_1 \approx 0.722/RC$, where R is the value of an internal fixed timing resistor of oscillator 94. A timing voltage waveform 104 at node 100 is typical of an RC oscillator that includes a CMOS 555 timer IC. Frequency $f_1$ of oscillator 94 is determined by detecting the frequency of positive current pulses on supply line 78 using conventional pulse detection circuitry. A complimentary pair of emitter followers comprising $T_1$ and $R_1$ and $T_2$ and $R_2$ respectively performs the function of a non-level shifting voltage follower. The emitter of transistor $T_2$ is connected to lead 106 connected to a driven shield 108 of capacitor 92, whereby substantially the identical voltage waveform developed at node 100 is also applied to driven shield 108. Shield 108 is located in a plane under and electrically insulated from electrodes 98 and 102 of capacitor 92.

Terminals of electrical components of oscillator 96 are connected to supply line 78 and ground trace 90 in reverse polarity to those of oscillator 94. Accordingly, when a voltage −V is applied to supply line 78, oscillator 96 is activated and oscillates at a square wave frequency $f_2$ inversely proportional to a resistance value of thermistor $R_T$. Oscillator 96 includes a fixed timing capacitor. Frequency $f_2$ of oscillator 96 is determined by detecting the frequency of negative current pulses on supply line 78. The unused square wave outputs not shown of oscillators 94 and 96 can be lightly capacitively loaded to increase the amplitudes of current pulses on line 78 to allow pulse detection without pre-amplification.

Many different types of circuits exist to measure capacitance to an accuracy between 5 and 50 ppm. For precision measurements, the capacitance value of planar capacitor 92 can be determined to an accuracy between 0.5 and 2 ppm using capacitance detection electronics disclosed in U.S. Pat. No. 6,456,477 and U.S. patent application Ser. Nos. 09/794,198, and 09/816,551. These circuit arrangements include a null-balanced bridge network with a sensing and reference capacitor. The bridge is balanced by high-gain current feedback that performs the function of a high-gain current servo. The reference capacitor of these and prior art capacitive measurement circuits may be a second planar capacitor of the present invention to provide the well-known advantages of detecting a change in a bridge network between two devices of substantially identical construction and temperature.

Based upon the general construction of planar capacitors 10, 26, and 40 of FIGS. 1, 2, and 3 respectively, it is evident planar capacitors and planar capacitance transducers can be constructed with multiple planar sensing and reference capacitors. At least one sensing and one reference capacitor can be formed on a top surface of a baselayer and a common shield formed on a bottom surface of the baselayer. Alternately, a planar sensing capacitor can be formed on a first surface of a first baselayer and a planar reference capacitor formed on a first surface of a second baselayer. For this alternative construction, a common driven shield can be located between the opposing second surfaces of said first and second baselayers. For both embodiments, it is desirable to place a thick portion of the coverlayer material over the reference capacitors to substantially restrict electric field coupling within this portion of the coverlayer.

FIG. 6A is a top view of a first metal layer 110 of flexible printed circuit transducer 76 laminated to a first side of a polyimide baselayer. Referring to FIG. 5, planar capacitor 92 is etched in a first region 112 and bottom-side circuit trace generally shown by reference numeral 114 is etched in an adjacent second region 116. Wire point pad 118 with a plated through hole 118' electrically connects supply line 78 to a portion of circuit trace 114 and to a portion of component-side circuit trace 120 on a second metal layer 122 shown in FIG. 6B. Wire point pad 124 with a plated through hole 124' electrically connects capacitor electrode 102 and a ground portion of circuit trace 114 to ground or a reference potential. Plated through hole 124' connects ground portions of trace 114 to ground portions of component-side circuit trace 120 on second metal layer 122.

FIG. 6B is a top view of second metal layer 122 of transducer 92 laminated to a second side of said baselayer. A driven shield 108 can be etched in a first region 112' or alternately the metal in this region can be removed. Component-side circuit features and trace 120 are etched in a second region 116'.

Figure 7:
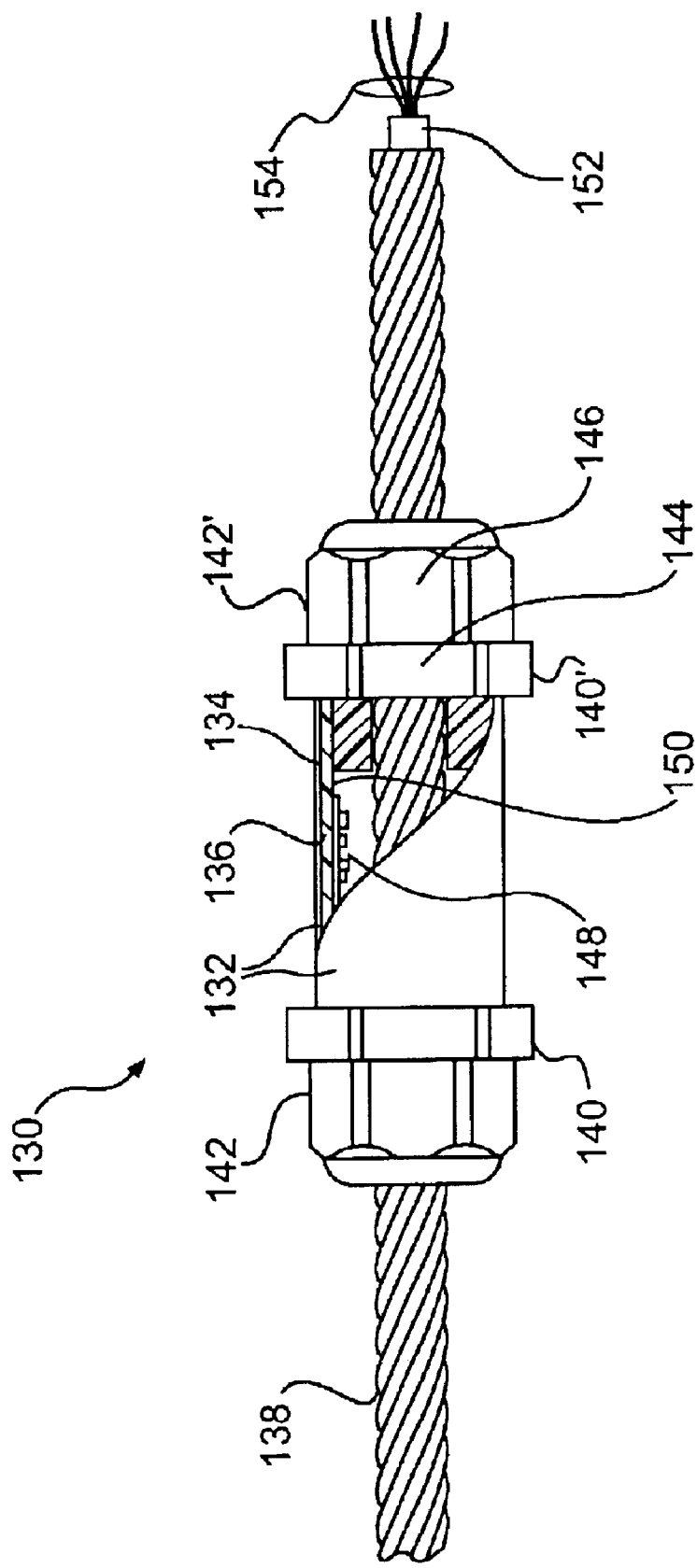
FIG. 7 is a view of a cable-bore moisture/temperature transducer.

FIG. 7, is a view a cable-bore transducer 130 developed to measure the moisture content and temperature of stored grain and other bulk products. A planar capacitor 132 with metal layers 42 and 44 of FIGS. 4A and 4B respectively is bonded to an outside surface 134 of a hollow polycarbonate tube 136 with metal layer 44 and driven shield 70 facing surface 134. Transducer 130 is secured to a stainless-steel cable 138 by polyamide endcap fittings 140 and 140' with dome nuts 142 and 142'. Endcap fittings 140 and 140' include overlapping clamping splines that tightly compress a polymeric sleeve around cable 138 with wrenching of dome nuts 142 and 142' using wrenching flats 144 and 146. Referring to FIGS. 4A and 5, wire points 60, 66, and 68 of capacitor 132 are electrically connected to a flexible circuit 148 adhered to an inside surface 150 of tube 136. Circuit 148 includes surface-mount electrical components of moisture/temperature sensing electronics. Cable 138 is typically a ¼ or ⅜ inch diameter, 6×7 or 6×19 wire rope of 402 stainless-steel fabricated around an extruded polyamide tube 152 loosely enclosing a group of insulated hookup wires 154. Two or more wires are extracted through a protective sleeve at each transducer site along cable 138. The wires connected to circuit 148 provide electrical power and transmit moisture/temperature data.

In an alternate embodiment of transducer 130, a planar capacitance transducer 76 of FIG. 5 with metal layers 110 and 122 of FIGS. 6A and 6B is bonded to tube 136 with metal layer 122 facing surface 134. Surface mount circuit region 116' of metal layer 122 is located on surface 134 within a recessed portion of endcap fitting 140.

Transducer 130 can be used to collect moisture and temperature data to control the fans of aeration systems at or in storage bins and silos. During an aeration cycle, multiple, cable-borne transducers provide data to determine the propagation of moisture and temperature fronts through the stored grain mass. These data can be used to conserve electrical power, detect condensation, and prevent a loss of market price due to over drying. Cable-borne sensors of the present invention have been constructed to detect insect infestation, molds, condensation, and spoilage in pockets of stored grain by detecting and correlating increases of moisture with temperature.

Figure 8:
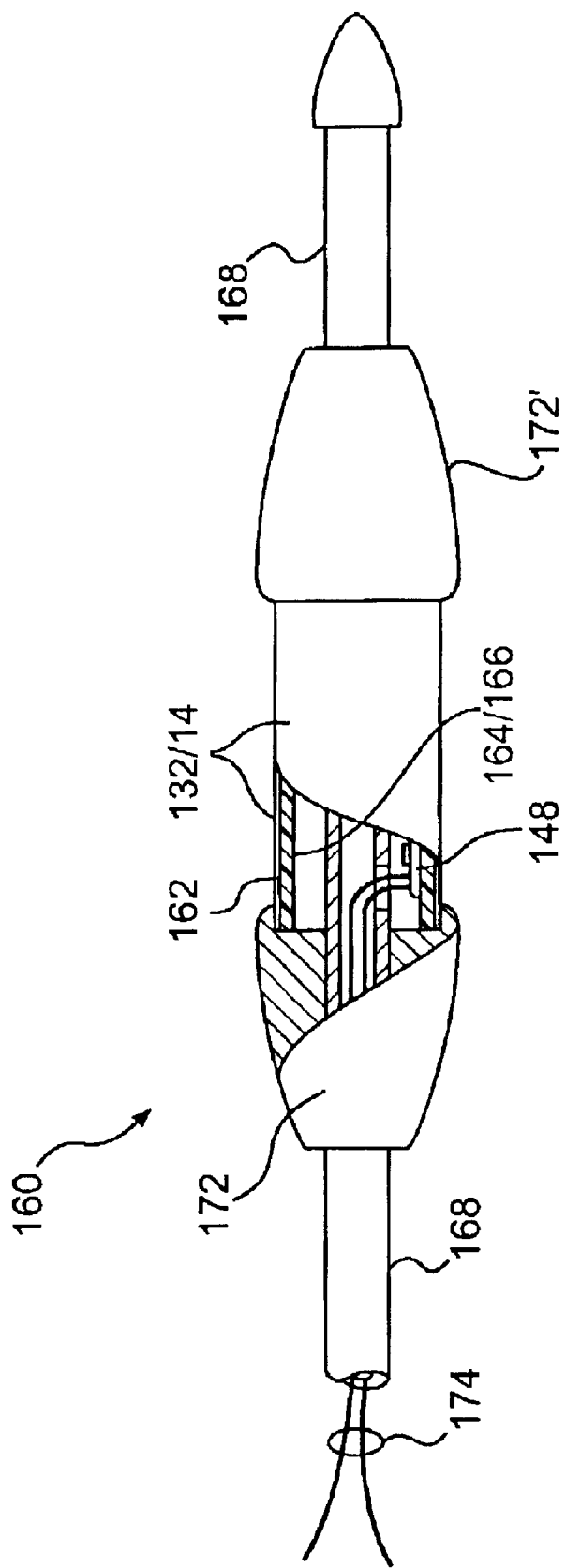
FIG. 8 is a view of a portion of a moisture/temperature measurement probe.

FIG. 8 is a view of a portion of a moisture and temperature measurement probe 160 developed to inspect grain. For this application, a flange on the shaft of the probe near a handle (not shown) allows the transducer to be inserted to a predetermined depth to provide measurement uniformity between measurements. Alternately, probe 160 can be used to measure the moisture content and temperature of soil for crop irrigation control to conserve water and improve crop quality. Probe 160 can be inserted in an augured hole in soil or in a back-filled trench.

Referring to FIG. 8, a planar capacitor 132 with metal layers 42 and 44 of FIGS. 4A and 4B respectively is bonded to an outside surface 162 of a hollow tube 164 with metal layer 44 and driven shield 70 facing surface 162. A flexible circuit 148 with moisture/temperature sensing electronics is bonded to an inside surface 166 of tube 164. Tube 164 is secured to a hollow metal rod 168 by endcaps 172 and 172'. A group of wires 174 routed through the center of rod 168 is connected to circuit 148 to provide electrical power and to transmit moisture/temperature data.

The material of the coverlayer of capacitor 132 is selected to have a smooth, low friction, and low free energy surface that is highly chemical resistant allow the probe to be easily cleaned with common detergents and solvents.

Figure 9:
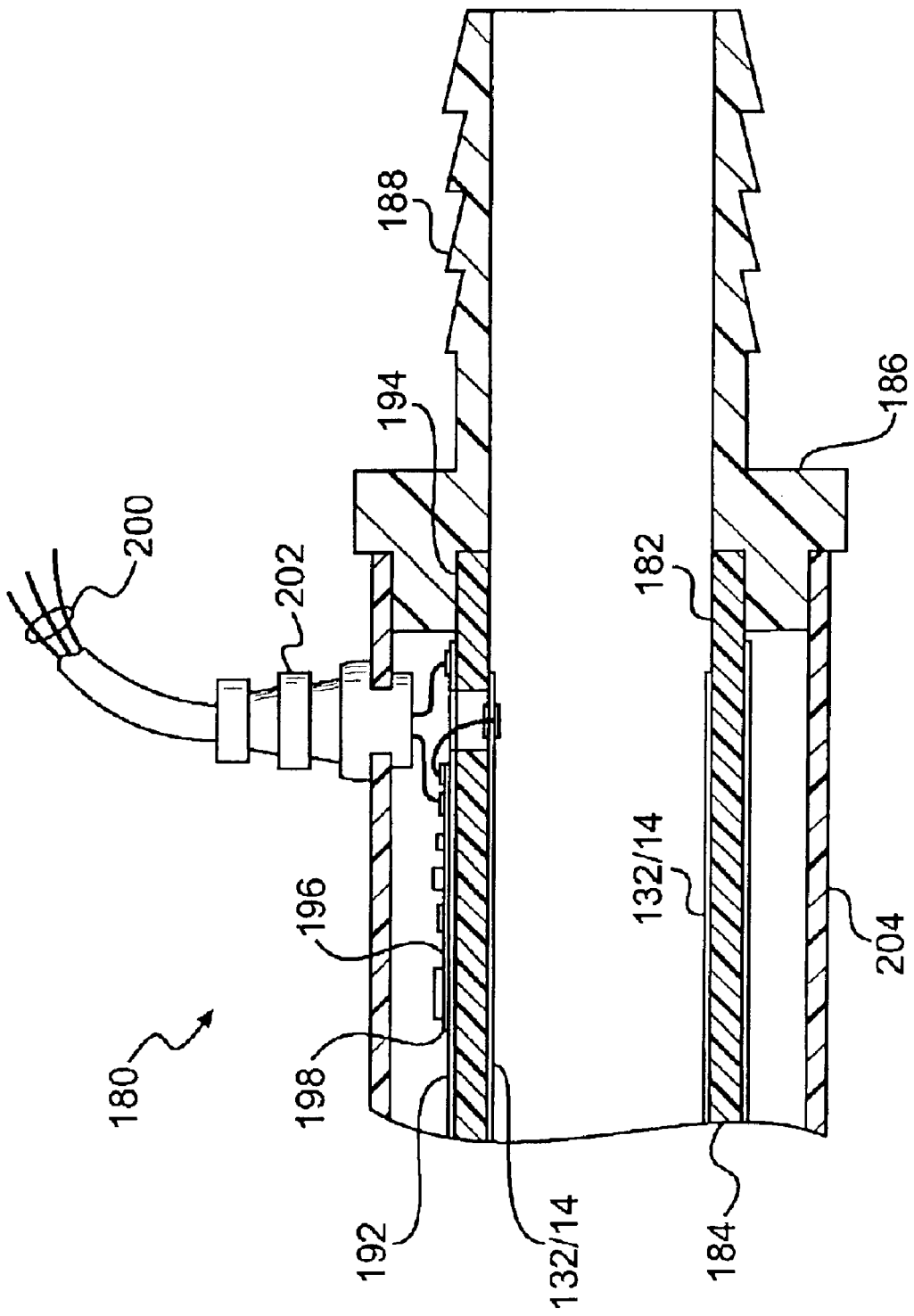
FIG. 9 is a partial view of an in-line airway humidity/temperature transducer.

FIG. 9 is partial sectional view of an in-line humidity and temperature transducer generally shown by reference numeral 180 that is inserted into a section of airway tubing of a respirator or anesthesia ventilator. Sensor 180 was developed to measure humidity during the cyclic inspiration and expiration of respiration. A planar capacitor 132 is bonded around an inside surface 182 of a tube 184. Tube 184 is connected between to two molded polyamide endcaps 186 with barbed extensions 188. A smooth cylindrical flange of an end portion of standard ribbed fluoropolymer tubing is connected to extensions 188. A thin-film, low-power polyimide heater 192 is bonded around an outside surface 194 of tube 184. Heater 192 of conventional construction includes a resistance element formed by etching a meander pattern in a nickel-alloy foil bonded to a polyimide baselayer. A flexible circuit 196 comprising humidity/temperature sensing electronics and a thermistor is bonded over a top surface portion 198 of heater 192. Capacitor 132 is electrically connected to circuit 196 that is electrically connected to external monitoring electronics by a group of wires 200 routed through a strain relief boot 202. Two leads connected to heater 192 are also routed through boot 202 to external temperature control electronics. Because of the scale of the drawing, electrical connections to capacitor 132, heater 192, and circuit 196 are shown representatively. An external cover 204 comprising a metal or metallized plastic tube is connected between and affixed to endcaps 186.

The capacitance of capacitor 132 is substantially a linear function of the water vapor content of gas flowing through sensor 180 at vapor pressure levels below a threshold of adsorption. However, a large change of capacitance occurs when the water vapor pressure of the gas reaches saturation and a film of water starts to condense on coverlayer 14. The relative humidity of expired air is high and near body temperature. A thermistor of circuit 196 is used to measure the interior temperature of sensor 180. The external electronics includes a conventional temperature control circuit that transduces the resistance of the thermistor and provides feedback current to heater 192 to maintain coverlayer 14 at a temperature at or above body temperature. Controlling the temperature of transducer 180 above body temperature provides the capability to make accurate and dynamic measurements the RH of inspiration and expiration. An advantage of in-line sensor 180 is it does not interfere with or provide resistance to gas flow and breathing. Another advantage is that all materials of sensor 180 can be selected to withstand autoclave temperatures and harsh disinfectants.

Smaller diameter in-line embodiments can measure water vapor in industrial gas and fuel lines and monitor the humidity of air drawn into intakes of combustion engines. Knowledge of the water content of a fuel mixture can be used to adjust engine timing and efficiency.

Coverlayer Materials

Coverlayers of transducers of the invention can be applied over a planar capacitor by processes including chemical vapor deposition (CVD), spin casting, and lamination. It is generally desirable the coverlayer material have low values of moisture absorption, surface free energy, permittivity, and dielectric dissipation compared to polyimide films and coatings.

Thin coverlayers of polyparaxylene (Parylene D, N, and F) are formed by a three-step CVD process. Parylene is a low dielectric, chemically inert, hydrophobic, and pin-hole free polymer. Film thicknesses between 0.3-$\mu$m to several hundred micrometers are routinely deposited. The friction of a Parylene surface is close to PTFE.

A coverlayer film of a copolymer of perfluoro-2,2-dimenthyl-1,3-dioxide with at least one fluoro comonomer (Teflon® AF) can be spin cast to form a coverlayer of a planar capacitive transducer. This material also can be applied by casting, spraying, painting, or dipping. After application, the coating is baked at a temperature between 100 and 200° C. to drive off solvent. Teflon AF is an amorphous fluoropolymer with the lowest dielectric constant of any common halopolymer. The material that can be formed in micron thick layers is sold under the trademark Teflon by DuPont.

Transducers of the invention can be constructed with thin films of a thermally processable plastic such as polycarbonate; polyethylene terephthalate; polyphenylene sulphide, and polypropylene. However, the preferred coverlayer material is generally a halocarbon or polyparaxylene. When a coverlayer is applied by lamination, it is desirable the material have a low melting temperature compared to 332–353° C. of polytetrafluoroethylene (PTFE) to minimize the cost and difficulty of fabrication. Suitable heat processable materials with approximate melting temperatures include a copolymer of tetrafluoroethylene and hexafluoropropylene (FEP) [260–280° C.]; polychlorotrifluoroethylene (PCTFE) [212° C.]; and a copolymer of vinylidenefluoride and chlorotrifluoroethylene (VF2/CTFE) [200° C.]. FEP has the best adhesion to metals, but certain applications are limited by its low tensile strength and wear resistance.

The specific details of the embodiments and methods described above are not intended to limit the scope of the appended claims and their legal equivalents.

What is claimed is:

1. A capacitive transducer comprising:
   a. a planar capacitor with at least two cooperating electrodes formed on a first surface of a dielectric baselayer with an opposing second surface;
   b. a thin dielectric coverlayer formed over said electrodes and an exposed surface of said coverlayer comprising a principal surface of said transducer;
   c. a material of said coverlayer having values of moisture absorption, surface free energy, permittivity, dielectric dissipation, and electrical conductance selected to maximize electric field coupling over said principal surface and within a region external to the surface;
   d. a time varying voltage from electronic measurement means connected across said cooperating electrodes, whereby capabilities are provided to rapidly measure capacitance, permittivity, dielectric dissipation, and a state of polarization of material adsorbed on and residing within said region external to said principal surface.

2. The transducer of claim 1 further including a driven shield with a first and second surface and said first surface affixed to said second surface of said baselayer and connected to same said time varying voltage, whereby electrical field coupling and associated fixed capacitance within and below said baselayer are minimized.

3. The transducer of claim 2 wherein said second surface of said driven shield is affixed to a means of temperature control.

4. The transducer of claim 1 further including a reference capacitor.

5. The transducer of claim 1 wherein said principal surface of said coverlayer comprises an activated surface.

6. The transducer of claim 1 wherein said coverlayer includes a material selected from the group comprising a fluoropolymer, chloropolymer, chlorofluoropolymer, and polyparaxylene.

7. The transducer of claim 1 wherein said coverlayer includes a thermally processable plastic.

8. A method to measure capacitance, permittivity, dielectric dissipation, and a state of polarization of material adsorbed on and residing within a region external to a principal surface. comprising the steps of:
   a. providing a planar capacitor with at least two thin cooperating electrodes formed on a first surface of a dielectric baselayer with an opposing second surface;
   b. providing a dielectric material with low values of moisture absorption, surface free energy, permittivity, and dielectric dissipation compared to polyimide films and coatings;
   c. forming from said dielectric material a thin coverlayer with a first surface applied over said capacitor electrodes and a second exposed surface comprising said principal surface;
   d. connecting a time varying voltage from electronic measurement means across the capacitor electrodes to provide an indication of measurement.

9. The method claim 8 further including the step of affixing a first surface of a driven shield with an opposing second surface to said second surface of said baselayer.

10. The method claim 9 further including the step of affixing said second surface of said driven shield to a means for temperature control.

11. The transducer of claim 8 wherein step a said planar capacitor is provided with a second pair of said at least two cooperating electrodes that comprise a reference capacitor.

12. The transducer of claim 8 further including after step c a step of activation to change a surface free energy of said principal surface.

13. A capacitive measurement means that electrically promotes a physical change in a material adsorbed on and residing within a region external to a principal surface and same said measurement means having a capability to detect and measure an effect of said physical change comprising:
   a. a planar capacitor with at least two cooperating electrodes formed on a first surface of a dielectric baselayer with an opposing second surface;
   b. a thin-film dielectric coverlayer formed over said electrodes and an exposed surface of said coverlayer comprising said principal surface;
   c. a material of said coverlayer having values of moisture absorption, surface free energy, permittivity, dielectric dissipation, and electrical conductance selected to maximize electric field coupling over and within a region external to said principal surface;
   d. a time varying voltage from electronic measurement means connected across said cooperating electrodes, whereby capabilities are provided to rapidly measure capacitance, permittivity, dielectric dissipation, and states of polarization, phase, and crystalline order of material on said principal surface and within said region external to the surface.

14. The transducer of claim 13 further including a driven shield with a first and second surface and said first surface affixed to said second surface of said baselayer and connected to same said time varying voltage.

15. The transducer of claim 14 wherein said second surface of said driven shield is affixed to a means of temperature control.

16. The transducer of claim 13 further including a reference capacitor.

17. The transducer of claim 13 wherein said principal surface of said coverlayer comprises an activated surface.

18. The transducer of claim 1 wherein said coverlayer includes a material selected from the group comprising a fluoropolymer, chloropolymer, chlorofluoropolymer, and polyparaxylene.

19. The transducer of claim 1 wherein said coverlayer includes a thermally processable plastic.

* * * * *